United States Patent

Nock et al.

Patent Number: 6,110,114
Date of Patent: Aug. 29, 2000

[54] FLEXIBLE BEAM SEQUENCING FOR 3-DIMENSIONAL ULTRASOUND IMAGING

[75] Inventors: Levin F. Nock, Bellevue; John C. Lazenby, Fall City, both of Wash.

[73] Assignee: Siemens Medical Systems, Inc., Iselin, N.J.

[21] Appl. No.: 09/163,866

[22] Filed: Sep. 30, 1998

[51] Int. Cl.⁷ ............................................. A61B 8/00
[52] U.S. Cl. ................................. 600/443; 128/916
[58] Field of Search .......................... 600/440–441, 600/443, 447, 453–55; 128/916

[56] References Cited

U.S. PATENT DOCUMENTS

| | | | |
|---|---|---|---|
| 5,282,471 | 2/1994 | Soto | 128/916 |
| 5,301,670 | 4/1994 | Soto et al. | 600/441 |
| 5,873,830 | 2/1999 | Hossack et al. | 600/447 |

*Primary Examiner*—Francis J. Jaworski

[57] ABSTRACT

A method of generating data compatible with forming a three-dimensional ultrasonic image includes selecting different frame rates for generating patterns of image information and frames of non-imaging information, such as motion information. The frame rates may be independently determined, based upon the desired characteristics of the two types of frames. Typically, image frames and motion frames are formed concurrently, with the formation of each motion frame overlapping the formation of more than one image frame, i.e., motion frames have a lower frame rate than image frames. After a sufficient number of image and motion frames have been generated, the image frames and the motion data are spatially coordinated to provide a three-dimensional flow image of a region of interest. In one approach, the spatial coordination of motion frames is implemented by incorporating the motion frames in a non-parallel relationship with the image frames. In a more accurate approach, the motion information is incorporated on a value-by-value basis into the image frames.

19 Claims, 3 Drawing Sheets

FLEXIBLE BEAM SEQUENCING FOR 3-DIMENSIONAL ULTRASOUND IMAGING

BACKGROUND OF THE INVENTION

The invention relates generally to ultrasonic imaging and more particularly to methods and systems for sequencing captures of data for generating at least two types of data frames.

DESCRIPTION OF THE RELATED ART

Medical ultrasound imaging systems may be used to display images of internal features of a patient. An acoustic transducer having an array of transducer elements is used to generate ultrasonic beams that propagate into the patient's body. Energy of the ultrasonic beams reflects off body tissues that present discontinuities or impedance changes to the propagating ultrasonic beams. The echoes from the tissues are sensed by the transducer and are converted into electrical signals that are amplified and decoded to form a cross-sectional image of the tissue. Ultrasound imaging systems provide physicians with real-time images of the internal features of the human anatomy without resorting to more invasive exploratory techniques, such as surgery.

Acoustic transducers which generate the ultrasonic beams typically include a piezoelectric element or a matrix of elements. Each piezoelectric element deforms in response to variations in the potential difference across the piezoelectric material, thereby producing the ultrasonic beams. Conventionally, the beams have a center frequency in the range of 2 to 15 MHz. The echoes from the tissues cause the piezoelectric element to deform and generate corresponding electrical signals. The electrical signals are collected to form a frame of image data. The frame is a multi-pixel array in which each pixel corresponds to a location in a two-dimensional view of the imaged tissue. Typically, the pixel values represent grey-scale values of the imaged tissue along a single plane.

A viewing device, such as a video display terminal, may be used to present the frame of image data as a cross-sectional slice of imaged tissue. The image aids a physician in diagnosing diseases and in comprehending the extent of internal injuries.

To further aid medical personnel, a three-dimensional ultrasonic image may be formed. Typically, this requires integrating a series of two-dimensional slices. The two-dimensional slices are acquired in one-by-one fashion, while the acoustic transducer is electronically and/or manually controlled to obtain two-dimensional slices at different positions. The slices are integrated to allow viewing of a volume of interest. The volume may be viewed as a volume rendering or surface rendering, and/or in three orthogonal planes (i.e., sagittal, transverse and frontal). Three-dimensional ultrasound systems are described in U.S. Pat. Nos. 5,782,766 to Weng et al. and 5,396,890 to Weng, each of which is assigned to the assignee of the present invention.

As a further aid to medical personnel, Doppler measurements may be acquired using the ultrasound system. The Doppler measurements can be used to determine a motion-related property, such as the velocity or power of blood flow and/or moving tissue. By acquiring and displaying Doppler shifts caused by blood flow, some relatively small anatomical defects can be detected without using more invasive techniques. The mode of operation of the ultrasound system in which Doppler shifts caused by blood flow are detected is sometimes referred to as "colorflow," since the Doppler shifts are often incorporated as color pixels into the grey-scale image information of the ultrasound system. For example, U.S. Pat. No. 5,443,071 to Banjanin et al. describes a colorflow imaging system in which motion toward the acoustic transducer is represented by the color red and motion away from the transducer is represented by the color blue. Each value of motion data is acquired by identifying differences in tissue positions over an "ensemble" of transmit-receive cycles. That is, a time series of pixel values is compared to detect the changes in tissue location during the time series. In a power mode, the same process is used, but the motion data of concern is the power contained in the time-variant part of the time series. As used below, "colorflow" and "Doppler" can refer to any of the known forms of velocity data or the power data.

Typically, the imaging interrogation beams for acquiring the grey-scale data have properties that are distinguishable from those of the motion interrogation beams for acquiring colorflow data. Image interrogation beams often have a shorter pulse length or a different frequency than motion interrogation beams. Moreover, the motion interrogation beams may be directed at an angle relative to the image interrogation beams. However, the image and motion interrogation beams may be identical with respect to beam transmissions and echo receptions, but processed differently after the echoes have been converted to electrical signals.

In generating a three-dimensional flow image, velocity-based information may be used to color code a three-dimensional image to distinguish motion away from a transducer from motion toward the transducer. For example, the image information may be represented by grey-scale values, motion toward the transducer may be indicated by the color red, and motion away from the transducer may be indicated by the color blue.

Since each pixel of motion data is a value that is acquired over a time interval, the color acquisition occupies most of the imaging time. The grey-scale acquisition requires a small percentage of the total time, but the grey-scale frame rate is limited by the color frame rate, since no grey-scale information is acquired during acquisition of the color data. Processing of relatively deep regions of interest may cause the frame rate to drop below ten frames per second. Preferably, the frame rate for grey-scale information is at least twenty frames per second.

The sample density of the color frame of motion data is typically less than the sample density of the grey-scale frame of image data. The color frame may require relatively few ultrasonic beams that are widely spaced, while the grey-scale frame may require many narrowly spaced ultrasonic beams. One of the main challenges of three-dimensional ultrasonic imaging is to provide adequate image quality in the third dimension (i.e., between consecutive image slices). If the slices are spaced too far apart, important image information may be missed between the slices. In order to avoid artifacts from the patient's respiratory motion, a three-dimensional volume should be acquired as rapidly as possible. The two requirements of rapid acquisition and closely spaced image slices can only be satisfied by a scanner having a high frame rate. The high frame rate is particularly important in ultrasound systems that rely on image data in order to deduce the position of each image frame, since geometric accuracy in assembling the acquired frames hinges upon having closely spaced frames.

Three-dimensional ultrasonic flow imaging operates reasonably well in some applications. However, for abdominal or obstetric imaging, the frame rate for acquiring the grey-scale frames and the color frames is insufficient, since abdominal motion is almost continuous.

As an alternative to motion data, other types of ultrasonically acquired information may be combined with multiple planes of image information. For example, a three-dimensional ultrasound image may be combined with one or more frames of data relating to temperature change or the presence of a contrast agent within the imaged region of interest. In some applications, data relating to strain, elastic properties and/or acoustic propagation speed are of interest and such data may be acquired acoustically for combination with multiple frames of image data. The ultrasonic acquisition of each of these types of information and the incorporation of the information into the image data carry the same concerns as the acquisition and utilization of motion data.

What is needed is a method that increases the flexibility of data acquisition within an ultrasound system that generates more than one type of data frame. As an example, the method should increase the flexibility of data acquisition for a system in which at least one frame of motion data is to be incorporated into a volume of image data to form a three-dimensional display in which movement is represented.

SUMMARY OF THE INVENTION

A method of generating data compatible with forming a multiplane ultrasound display of at least two characteristics of an interrogated volume includes selecting different frame rates for concurrently generating different types of frames of ultrasonically acquired data. The concurrent generation of two different types of frames is achieved by interspersing captures of first-characteristic information with captures of second-characteristic information. The first-characteristic information may be image information, while the second-characteristic may be related to a property such as motion (e.g., power or velocity), temperature change, strain, elasticity, acoustic propagation speed, or the presence of a contrast agent within the interrogated volume. In the preferred embodiment, the frame rate of acquiring image frames is greater than the frame rate of acquiring the second-characteristic information. The image information and the second-characteristic information are then spatially coordinated to provide a three-dimensional image of the interrogated volume, with indications of the second characteristic of the volume.

In the preferred embodiment, the first type of frame is an image frame and the second type of frame is a motion frame. Each image frame may be an array of grey-scale pixel values. The image frames are combined as slices in order to generate the three-dimensional image of the interrogated volume. A high resolution can be achieved by providing a high frame rate, since the slices of image data will be close together, avoiding missing image information. Moreover, the position of the slices can be more accurately estimated when the slices are closely spaced, thereby increasing the reliability of three-dimensional reconstruction of both types of information. The motion data may be generated as color values that are indicative of power or velocity of motion within the interrogated volume. In this embodiment, the second-characteristic frames provide colorflow representations within the three-dimensional image.

Because the image frame rate is greater than the second-characteristic frame rate, spatially coordinating the two types of information is a concern. In one embodiment, each second-characteristic frame is combined with the image frames as a slice that is non-parallel to the image slices. For example, the start "edge" of a motion frame may be coordinated with the image slice that was being formed at the outset of the formation of the motion frame, while the end "edge" may be coordinated with the image slice being formed at the conclusion of the motion frame. In a second embodiment of the spatial coordination, the second-characteristic information is incorporated into the three-dimensional image on a value-by-value basis. This second embodiment is preferred in applications in which the process occurs in real time and in applications in which independent location information is available for mapping purposes.

By determining the utilization of ultrasound transmissions and echo signal processing on a beam-by-beam basis, rather than a frame-by-frame basis, sampling densities can be controlled independently in the third dimension and optimized for each of the two or more characteristics of interest. For example, in a color-coding application, if two interrogation beams are utilized to acquire grey-scale image information between each determination of second-characteristic information (e.g., motion data), the frame rate of the image frames will be twice that of the colorflow frames, if the number of pixels in a colorflow frame equals the number of pixels in a grey-scale frame.

DETAILED DESCRIPTION

Figure 1:
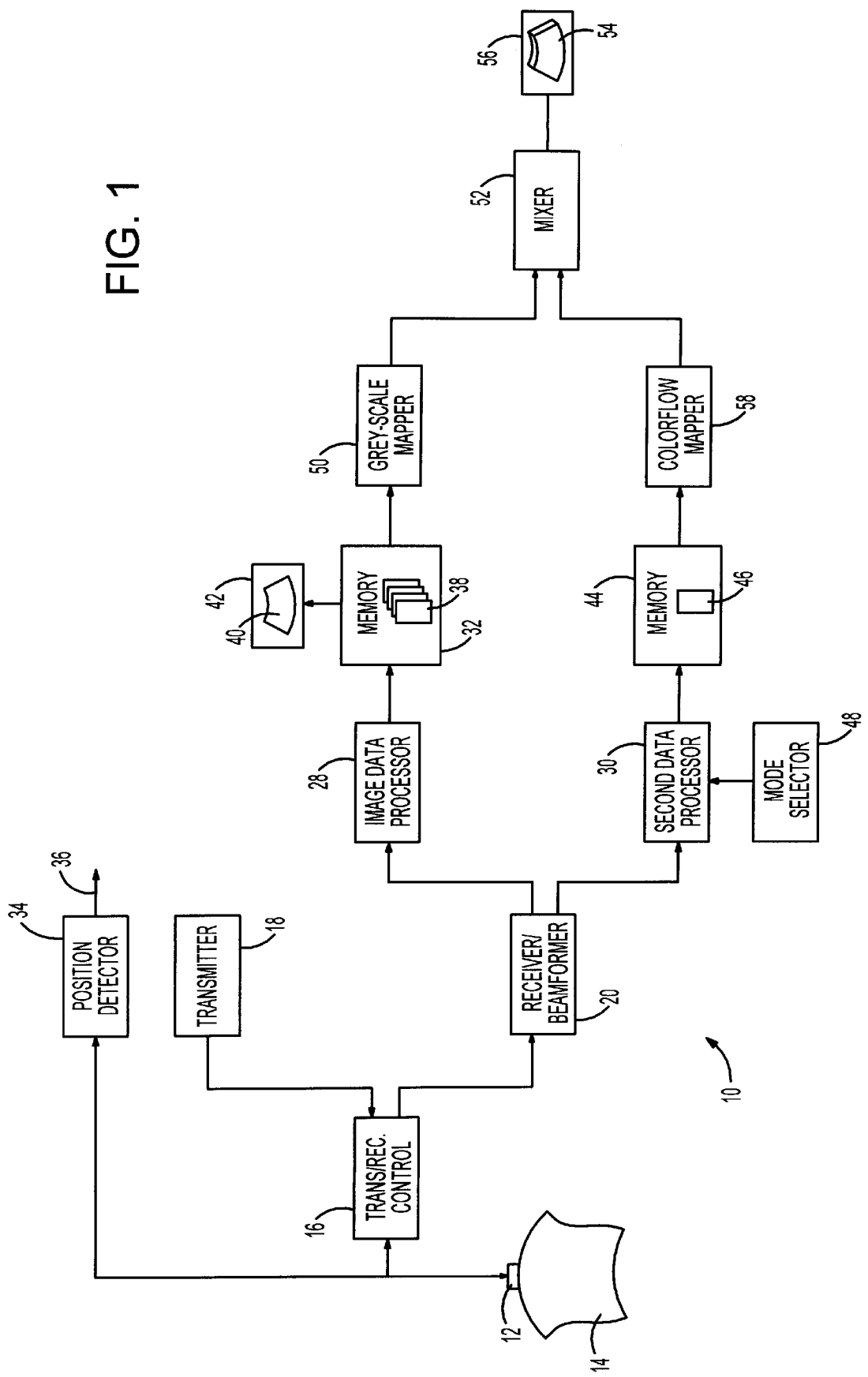
FIG. 1 is a block diagram of components of an ultrasound system that allows flexible beam sequencing in accordance with the invention.

With reference to FIG. 1, an ultrasound imaging system 10 is shown as including a transducer 12 in contact with the skin of a patient 14. The structure of the transducer 12 is not critical to the invention. In one embodiment, the transducer includes an array of 192 piezoelectric elements that are used to generate ultrasonic beams. An ultrasonic beam may be steered and focused using techniques well known in the art. By detecting reflections from a region of interest (i.e., interrogated volume) within the patient 14, the region can be imaged. Interspersing image interrogation beams and motion interrogation beams enables the system to be used to form a three-dimensional image that is color coded to indicate movement within the regions of interest. Typically, the movement is caused by blood flow. As alternatives to acquiring image information and/or motion information, echoes from the transmissions of interrogation beams can be processed to acquire frames of data relating to other characteristics of the interrogated volume. For example, the characteristics of concern may be image data combined with one or more of temperature variations, strain, elasticity, acoustic propagation speed and the presence of a contrast agent. However, for simplicity with respect to description of the invention, the first characteristic of concern will be identified as image data for generating image frames and the second characteristic of concern will be identified as motion data for generating motion frames.

A transmitter/receiver control device 16 alternates between connecting the transducer 12 with a transmitter 18 and with a receiver/beamformer 20. The transmitter 18 provides electrical signals to the transducer for generating ultrasonic beams. An acoustically conductive lubricating agent may be applied to the skin of the patient 14 to improve acoustic coupling between the transducer and the patient. The ultrasonic beams propagate into the patient and are reflected by anatomical features, such as blood vessels. Echoes return through the skin to the transducer and are converted to electrical signals that are directed to the receiver/beamformer by the control device 16. The control device isolates the sensitive circuitry of the receiver/beamformer from the circuitry of the transmitter 18.

The echoes received from the transducer 12 include echoes from tissue and from blood flow in vessels. The weak ultrasonic echoes are converted to electrical signals by the transducer and sent to the receiver/beamformer 20 for amplification. The beam forming is typically a digital process, so that an analog-to-digital converter is required.

The combination of the transmitter 18 and the control device 16 has two modes of operation. In a first mode, the transducer 12 is caused to generate interrogation beams that are to be used for detecting tissue, while in a second mode the transducer is caused to generate interrogation beams that are to be used for detecting movement within the region of interest. Image interrogation beams generated during operation in the first mode often have properties that are distinguishable from properties of motion interrogation beams generated during operation of the system 10 in the second mode. However, this is not critical to the invention, since the image and motion interrogation beams may be identical with respect to transmission characteristics, as long as the echo signals are processed differently, depending upon whether the echo signals are to be used to acquire image or motion information.

Figure 2:
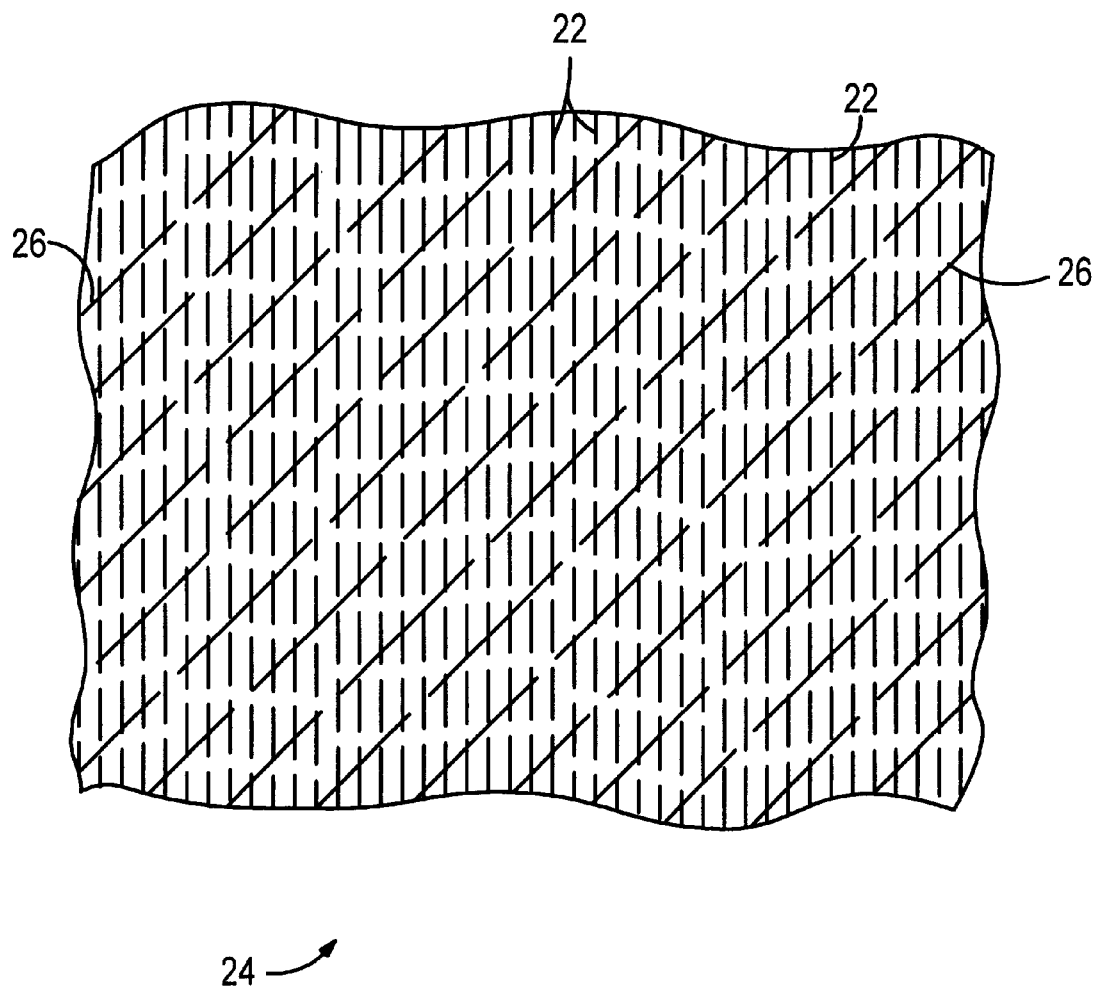
FIG. 2 is a schematic view of a set of parallel imaging interrogation beams and a set of motion interrogation beams for forming a three-dimensional ultrasonic flow image in accordance with the invention.

Referring to FIG. 2, the image interrogation beams 22 are shown as being projected into the region of interest 24 with a relatively high sample density. That is, the image interrogation beams are relatively closely spaced. In comparison, motion interrogation beams 26 may be further apart. Conventionally, the image interrogation beams 22 have a direction that is perpendicular to the transducer, since the acquisition of image data is dependent upon sensing echoes from tissue. The motion interrogation beams 26 may be perpendicular to the transducer, or may be directed at an acute angle to the transducer, since the motion information that is acquired is partially based on the angle between the beam 26 and the anatomical feature that is in motion. As is well known in the art, when a motion interrogation beam 26 is dispersed by flowing blood cells, the frequency of the beam is subjected to Doppler shift. Echo signals are processed to determine the velocity, speed and/or direction of motion.

There may be other properties that may distinguish the image interrogation beams 22 from the motion interrogation beams 26. The duty cycle of the transmitter 18 may be longer for the transmission of motion interrogation beams. For example, the motion interrogation beam 26 may be ten cycles of a 5 MHz signal, while an image interrogation beam may be two or three cycles of the 5 MHz signal. If the transducer 12 allows, the frequencies can be different for the two types of beams. As previously noted, the sample density of the motion interrogation beams is typically less than the sample density of the image interrogation beams. However, the invention to be described below may be used in systems in which the image interrogation beams are identical to the motion interrogation beams.

Again referring to FIG. 1, the image information is directed to an image data processor 28 and the motion information is directed to a Doppler data processor 30. Frames of two-dimensional image information are acquired by memory 32 and are stored as arrays of pixel values. While not critical, the pixel values may be representative of a grey-scale image of one plane of the region of interest. The two-dimensional images are acquired in real-time, during movement of the transducer 12 relative to the patient 14. The movement may be provided by an automated device or by a manual control of the operator. Optionally, a position detector 34 may be included to indicate the current transducer position. The detector has an output 36 that is accessible by any of the components of the ultrasound imaging system 10 that require position information for processing. However, ultrasound imaging systems that do not include a position detector are known in the art.

The memory 32 stores a number of grey-scale frames. Four such frames 38 are shown in FIG. 1. Each frame is a cross section along a different plane of the patient 14. One cross sectional image 40 of the region of interest is shown at a monitor 42 connected to memory 32. A multiplane image (i.e., three-dimensional image) is possible by combining the frames 38, as will be described below.

The second data processor 30 is connected to memory 44 for generating a frame 46 of motion data. The frame may be a pixel array of color-coding values. The processor 30 may operate in a velocity-based mode or a power-based mode. Alternatively, other motion-related criteria may be determined by the processor 30, or a characteristic unrelated to motion (e.g., temperature variations) may be determined. A mode selector 48 is used to select the desired operation for forming the frame 46 of motion data.

As is known in the art, for each pixel value, the second data processor 30 performs algorithmic operations on an ensemble of echo signals. Samples from a given depth are taken at a pulse repetition frequency that is determined by the rate of transmissions of motion interrogation beams by the transducer 12. The process is described in detail in U.S. Pat. No. 5,443,071 to Banjanin et al., which is assigned to the assignee of the present invention.

FLEXIBLE BEAM SEQUENCING

In accordance with the invention, the utilization of echoes from interrogation beams to form the image frames 38 or the second-characteristic frames 46 (e.g., motion frames) is determined on a beam-by-beam basis. That is, the frame rates for acquiring the image frames 38 and the second-characteristic frames 46 are independently selected and the two types of frames are concurrently acquired. For example, during the time that memory 44 stores the motion data to generate the single motion frame 46, the four frames 38 of image data may be acquired. Typically, high resolution three-dimensional ultrasonic imaging requires a greater number of image frames than motion frames. In order to generate the three-dimensional image of the region of interest, the image frames 38 are spatially coordinated. Each pixel is converted to a physical position in the patient coordinate system and is reprojected into a volume data set. In the system 10 of FIG. 1, the grey-scale mapper 50 and the mixer 52 cooperate to provide the conversion and reprojection into a volume data set that is capable of providing a three-dimensional image 54 at a monitor 56. The frame-to-volume process may require interpolation of data between patient slices, using computer software. The accuracy of the interpolation depends partly upon the density of image frames 38 for forming the three-dimensional display 54.

By selecting the image frame rate independently of the second-characteristic frame rate, the sampling densities can be individually controlled in the third dimension. Moreover, frame acquisition can be optimized for each mode.

In the four-to-one ratio of acquiring image frames 38 to motion frames 46, four beams may be used to acquire image information between each pair of motion data determinations. As a result, the transducer 12 may have moved a significant distance during the time that the motion frame 46 was acquired. Colorflow data is projected into the volume of grey-scale data to provide an indication of power or velocity of motion within the region of interest. Because the image frame rate is greater than the motion frame rate, spatially coordinating the motion data to the image data is a concern. The same concern is likely to exist if the more slowly acquired frames store second-characteristic data other than motion data, such as data from tissue elastography. In one embodiment of the spatial coordination of the data, each second-characteristic frame is combined with the image frame as a slice that is not parallel to the image slices. For example, the start "edge" of a second-characteristic frame may be coordinated with the image slice that was being formed at the outset of the formation of the second-characteristic frame. At the opposite "edge" of the second-characteristic frame, the frame may be coordinated with the image slice that was formed at the conclusion of the second-characteristic frame. This operation may be performed by the colorflow mapper 58 and the mixer 52.

An alternative embodiment of spatially coordinating a "frame" of second-characteristic information to the image slices of the volume set is to incorporate the information on a value-by-value basis. As previously noted, the colorflow value of motion data is derived from an ensemble of echo signals. Particularly within applications in which the transducer position information is available from the position detector 34, each value of motion data may be incorporated into the volume data set as the colorflow value is determined. This second approach of incorporating the motion information is more accurate than the approach of incorporating an intact frame of motion information in non-parallel relationship with slices of image information.

Figure 3:
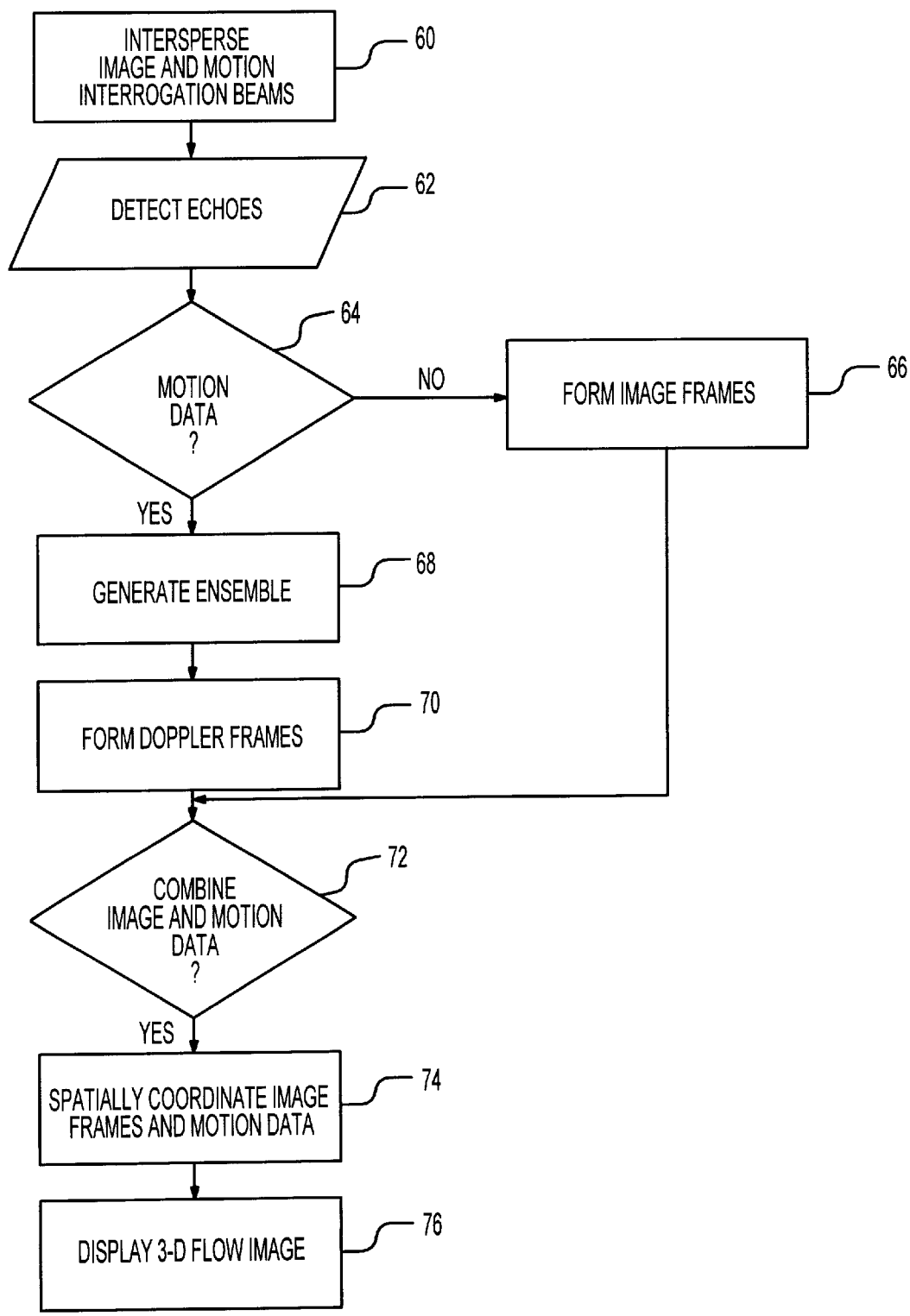
FIG. 3 is a process flow of steps for generating the three-dimensional ultrasonic flow image using the system of FIG. 1.

With reference to FIGS. 1 and 3, the process for generating the three-dimensional ultrasonic flow image 54 at the monitor 56 includes the step 60 of interspersing image and motion interrogation beams. As previously noted, this step is distinguishable from conventional techniques, since image frames 38 and motion frames 46 are concurrently acquired and are formed at different frame rates. As an example, four image frames 38 may be formed during the acquisition of a single motion frame 46, with four image interrogation beams being transmitted between successive acquisitions of motion data for the motion frame. However, the interspersion of image and motion interrogation beams may follow other patterns. As another example, two beams of motion data may be acquired successively, followed by determination of eight beams of image information.

In step 62, the echoes from anatomical features within the patient 14 are received by the transducer 12. Determination step 64 separates echoes of image interrogation beams from echoes of motion interrogation beams. If a particular echo is to be processed as image information, the echo is used in step 66 to form one of the image frames. On the other hand, if the echo is to be processed to acquire motion information, the echo is used with other echoes to generate an ensemble at step 68 for calculating a pixel value of motion information. The calculated motion information is used at step 70 to form a motion frame.

In decision step 72, a determination is made as to whether to combine the frames 38 of image information with the frames 46 of motion information. The spatial coordination of image frames from memory 32 may be executed using known techniques and the spatial coordination of the motion data may be executed using either of the two approaches described above. That is, each slice of motion information may be placed in a non-parallel relationship with the image frames, or the motion information may be incorporated into the image frames on a value-by-value basis.

The three-dimensional image is displayed in step 76, using the monitor 56. Alternatively, other techniques may be used by medical personnel. For example, the spatially coordinated image and motion data may be employed to provide a printout of the scanned region of interest of the patient 12.

What is claimed is:

1. A method of generating data compatible with forming an ultrasound image comprising steps of:

forming a plurality of first frames of data at a first frame rate, including transmitting first acoustic beams to a region of interest and receiving first echo beams therefrom, said data of said first frames being responsive to said first echo beams and being representative of a first characteristic of said region of interest;

forming at least one second frame of data at a second frame rate, including transmitting second acoustic beams to said region of interest and receiving second echo beams therefrom, said data of each said second frame being responsive to said second echo beams and being representative of a second characteristic of said region of interest, said formation of each said second frame being executed concurrently with said formation of said first frames such that transmissions and receptions of said first acoustic and echo beams to form a particular first frame are interspersed with transmissions and receptions of said second acoustic and echo beams to form said each second frame, said first frame rate being greater than said second frame rate; and combining said first and second frames to form a multiplane ultrasound representation of said first and second characteristics, including distributing data from each said second frame among a plurality of said first frames such that said data of said first and second frames are spatially correlated.

2. The method of claim 1 wherein said step of combining said first and second frames includes forming a three-dimensional display of said region of interest based on said first frames and includes coding said three-dimensional display based upon said at least one second frame.

3. The method of claim 2 wherein said step of forming said second frames includes transmitting said second acoustic beams as motion interrogation beams and includes determining power or velocities of motions within said region of interest based upon a time series of said second echo beams, said motion interrogation beams being distinguishable from said first acoustic beams.

4. The method of claim 2 wherein said step of forming said three-dimensional display includes spatially coordinating said data of said at least one second frame into said three-dimensional image in a value-by-value approach, each said second frame being an array of values of said motion data, said value-by-value approach including adding each value of said array to said three-dimensional representation based upon interpolations from position information relating to acquiring said motion data of said each value, thereby spatially correlating each said value with said three-dimensional image.

5. The method of claim 2 wherein said step of forming said three-dimensional display includes combining said first frames as slices of image data and incorporating each said second frame in a position based upon positions of a plurality of first frames formed concurrently with forming said each second frame, such that said data of each said second frame is spatially coordinated with data of those first frames with which there was concurrent data acquisition.

6. The method of claim 1 further comprising a step of independently selecting said first and second frame rates based upon achieving identified sampling densities of said first and second frames, said steps of forming said first and second frames including shifting between transmitting said first and second acoustic beams such that said first and second frames are concurrently formed while maintaining said independently selected first and second frame rates, said step of combining said first and second frames including displaying said first and second frames at display rates that substantially match said first and second frame rates.

7. The method of claim 6 wherein said step of independently selecting said first and second frame rates includes designating said first frame rate to be sufficiently greater than said second frame rate such that more than one first frame is formed concurrently with formation of each second frame.

8. The method of claim 1 wherein said first acoustic beams are distinguishable from said second acoustic beams with respect to at least one of direction of propagation and pulse length.

9. The method of claim 8 wherein said steps of transmitting said first and second acoustic beams utilize a single ultrasonic transducer, said data of said first frames being in a form of grey-scale values, said data of said second frames being in a form of color values.

10. A method of forming an image of a region of interest in which movement occurs, said method comprising steps of:

transmitting a plurality of interrogation beams to said region of interest by means of an ultrasonic transducer;

forming image frames of imaging information of said region of interest based upon echoes of said interrogation beams;

forming second frames of motion data representative of said motion within said region of interest, including basing said motion data on echoes of said interrogation beams, said second frames being formed simultaneously with said image frames such that formation of each said second frame overlaps formation of more than one said image frame; and spatially coordinating said image frames and said motion data to provide a three-dimensional image of said region of interest having indications of said motion within said region of interest, including correlating each said second frame with at least two said image frames with which there was overlap in formation.

11. The method of claim 10 further comprising a step of displaying said three-dimensional image using said imaging information to determine grey-scale data and using said motion data to determine color data.

12. The method of claim 10 wherein said steps of forming said image and second frames include assembling arrays of pixel values, said pixel values of each said second frame being based upon a time series of acquiring said echoes.

13. The method of claim 12 wherein said step of spatially coordinating said image frames and said motion data includes incorporating said motion data on a value-by-value basis such that a location of a particular pixel value within said three-dimensional display is based upon a spatial coordination of motion represented by said particular pixel value, including using each said pixel value of said second frames at only one location in said three-dimensional image.

14. A system for forming an image of a region of interest comprising:

a transducer means for generating acoustic energy and detecting echoes of said acoustic energy;

first frame-forming means for acquiring two-dimensional image frames of image data based upon echoes received by said transducer means;

second frame-forming means for acquiring two-dimensional second frames of characteristic data based upon echoes received by said transducer means, said characteristic data being distinguishable from said image data;

controller means, connected to said transducer means, for interleaving utilization of said echoes by said first and second frame-forming means on a beam-by-beam basis such that acquiring each second frame overlaps more than one image frame; and processing means for interleaving utilization of each said second frames with more than one image frame with which there is overlap so as to form a three-dimensional image of said region of interest from said image frames and said second frames.

15. The system of claim 14 wherein said controller means is configured to switch said transducer means between connections with said first and second frame-forming means to provide concurrent acquisitions of said image and second frames by said first and second frame-forming means.

16. The system of claim 14 wherein said transducer means is configured such that image interrogation beams generated by said transducer for utilization by said first frame-forming means have beam properties that distinguish said image beams from motion interrogation beams generated by said transducer for utilization by said second frame-forming means.

17. The system of claim 14 wherein said processing means is enabled to spatially coordinate said image frames and to spatially coordinate individual values of each said second frames to a plurality of said spatially coordinated image frames.

18. The system of claim 14 further comprising a means for displaying said three-dimensional image such that said characteristic data of said second frames is represented by color coding, said characteristic data being motion data.

19. The system of claim 18 wherein said first frame-forming means stores said image frames as pixel values of grey-scale data representative of said region of interest, said second frame-forming means storing said second frames as pixel values of color data representative of motion within said region of interest.

* * * * *